United States Patent [19]

Shimonaka et al.

[11] Patent Number: 4,736,732

[45] Date of Patent: Apr. 12, 1988

[54] ENDOSCOPIC FLUID CHANGING DEVICE

[75] Inventors: Hideki Shimonaka; Yosuke Yoshimoto; Masaaki Nakazawa, all of Hachioji, Japan

[73] Assignee: Olympus Optical Co., Ltd., Japan

[21] Appl. No.: 902,193

[22] Filed: Aug. 29, 1986

[30] Foreign Application Priority Data

Sep. 3, 1985 [JP] Japan .................. 60-194361
Aug. 14, 1986 [JP] Japan .................. 61-190924

[51] Int. Cl.⁴ .............................................. A61B 1/12
[52] U.S. Cl. ................................................... 128/4
[58] Field of Search ........................................ 128/4, 6

[56] References Cited

U.S. PATENT DOCUMENTS

| | | | |
|---|---|---|---|
| 4,198,958 | 4/1980 | Utsugi | 128/4 X |
| 4,412,531 | 1/1983 | Chikashige | 128/4 |
| 4,469,090 | 4/1984 | Konomura | 128/4 |
| 4,489,712 | 12/1984 | Ohshima | 128/6 |
| 4,509,507 | 4/1985 | Yabe | 128/4 |
| 4,537,182 | 8/1985 | Otani | 128/4 |
| 4,537,209 | 8/1985 | Sasa | 128/4 X |
| 4,561,428 | 12/1985 | Konomura | 128/4 |

FOREIGN PATENT DOCUMENTS

| | | |
|---|---|---|
| 1566561 | 4/1971 | Fed. Rep. of Germany . |
| 2441082 | 4/1975 | Fed. Rep. of Germany . |
| 3237777 | 5/1983 | Fed. Rep. of Germany . |
| 57-103621 | 6/1982 | Japan . |
| 569441 | 3/1983 | Japan . |
| 6023001 | 2/1985 | Japan . |

Primary Examiner—William H. Grieb

[57] ABSTRACT

Disclosed is a construction of an endoscopic fluid changing device which, attached to an endoscope, regulates the flow of a fluid in a channel of the endoscope. The fluid changing device comprises a cylindrical casing having a suction port, in the side wall thereof, a channel pipe provided in the center of the casing, and having an opening at the upper end portion thereof, the lower end portion of the channel pipe being connected to an instrument channel, extending to the distal end portion of the endoscope, a cap member covering the opening of the channel pipe, a piston disposed between the casing and the channel pipe, and capable of vertical motion, a spring for urging the piston upward, first valve device provided at the upper portion of the piston, and adapted to open or close a first passage as the piston is operated, the first passage extending from the suction port to the outside of the casing, and second valve device provided at the lower portion of the piston, and adapted to close or open a second passage, in contrast with the first passage, as the piston is operated, the second passage extending from the suction port to the instrument channel.

16 Claims, 10 Drawing Sheets

ENDOSCOPIC FLUID CHANGING DEVICE

BACKGROUND OF THE INVENTION

A. Field of the Invention

The present invention relates to a fluid changing device for changing a channel in an endoscope, thereby regulating the flow of a fluid in the channel.

B. Description of the Prior Art (a) Generally known as an example of a conventional endoscopic fluid changing device is a suction adjusting device which is disclosed in Japanese Utility Model Publication No. 56-9441. This device is built in an opening portion of an endoscope, in which a medical instrument is to be inserted. In this suction adjusting device, a cylindrical casing is fluidly connected to an instrument channel, and a suction port, connecting with a suction unit, is formed in the middle portion of the side wall of the casing. An inner cylinder is fixed inside the casing. It contains a slide valve for controlling the suction port. Normally, the valve is open, so that an opening portion of the casing and the suction unit are fluidly connected, thus reducing the load of a suction pump, in the suction unit. In sucking filth or the like from the body cavity, through the instrument channel, an operator closes the opening portion of the casing, with his finger, to effect suction. In feeding a liquid into the body cavity, through the opening portion and the channel, moreover, the slide valve is shifted to close the suction port.

(b) In a suction adjusting device stated in Japanese Utility Model Disclosure No. 60-23001, a valve seat is formed on the bottom portion of a cylindrical casing, and an elastic valve member is disposed in the casing. In feeding a liquid into the body cavity, a passage for suction is closed by means of the elastic valve.

(c) Conventional passage changing means, as stated, for example, in Japanese Patent Disclosure No. 57-103621, comprises a cylinder with a suction port in its side wall, and a piston with an O-ring thereon. A passage is changed by sliding the piston in the cylinder.

In prior art systems (a) and (b), the operator must close the opening portion (relief port) with his finger, during the suction. Therefore, filth or other matter, sucked from the body cavity through the instrument channel, may possibly reach the relief port, thus soiling the operator's finger. This is not very sanitary.

When the filth or other matter is not expected to be sucked from the body cavity, moreover, it can be sucked little by little, through the instrument channel, although the opening portion of the casing is open. If the endoscope is inserted, for example, in a bronchial tube, therefore, the matter may possibly prevent a patient from breathing well. If the stomach or other internal organ is inflated with air, introduced through the endoscope inserted in the organ, for observation, the air will be able to flow out of the organ, through the opening portion, thereby preventing a satisfactory observation.

SUMMARY OF THE INVENTION

An object of the present invention is to provide an endoscopic fluid changing device, in which a sucking action in an instrument channel is stopped completely when filth or other matter need not be sucked from the body cavity, and a liquid cannot be sucked into a suction pump while it is being fed into the body cavity.

Another object of the invention is to improve the durability of a valve member of an endoscopic fluid changing device, and to reduce the manufacturing costs of the device.

A further object of the present invention is to make compact an endoscopic fluid changing device, and to make compact an operating section of the endoscope.

The above objects of the invention are achieved by an endoscopic fluid changing device, which comprises a cylindrical casing having a suction port, in the side wall thereof; a channel pipe provided in the center of the casing, and having an opening at the upper end portion thereof, the lower end portion of the channel pipe being connected to an instrument channel, extending to the distal end portion of an endoscope; a cap member covering the opening of the channel pipe; a piston disposed between the casing and the channel pipe, and capable of vertical motion; a spring for urging the piston upward; first valve means provided at the upper portion of the piston, and adapted to open or close a first passage as the piston is operated, the first passage extending from the suction port to the outside of the casing; and second valve means provided at the lower portion of the piston, and adapted to close or open a second passage, in contrast with the first passage, as the piston is operated, the second passage extending from the suction port to the instrument channel.

In another aspect of the invention, the endoscopic fluid changing device comprises a cylindrical casing having a suction port, in the side wall thereof; a cylinder having a flange portion formed with a plurality of vent holes, and mounted inside the casing by means of the flange portion; a piston disposed in the cylinder and capable of vertical motion; a spring for urging the piston upward; first valve means provided at the upper portion of the cylinder, and adapted to open or close a first passage as the piston is operated, the first passage extending from the suction port to the outside of the casing, via the vent holes; and second valve means provided at the lower portion of the cylinder, and adapted to close or open a second passage, in contrast with the first passage, as the piston is operated, the second passage extending from the suction port to the instrument channel.

DETAILED DESCRIPTION OF THE PREFERRED EMBODIMENTS

Several embodiments of the present invention will now be described in detail, with reference to the accompanying drawings.

Figure 1:
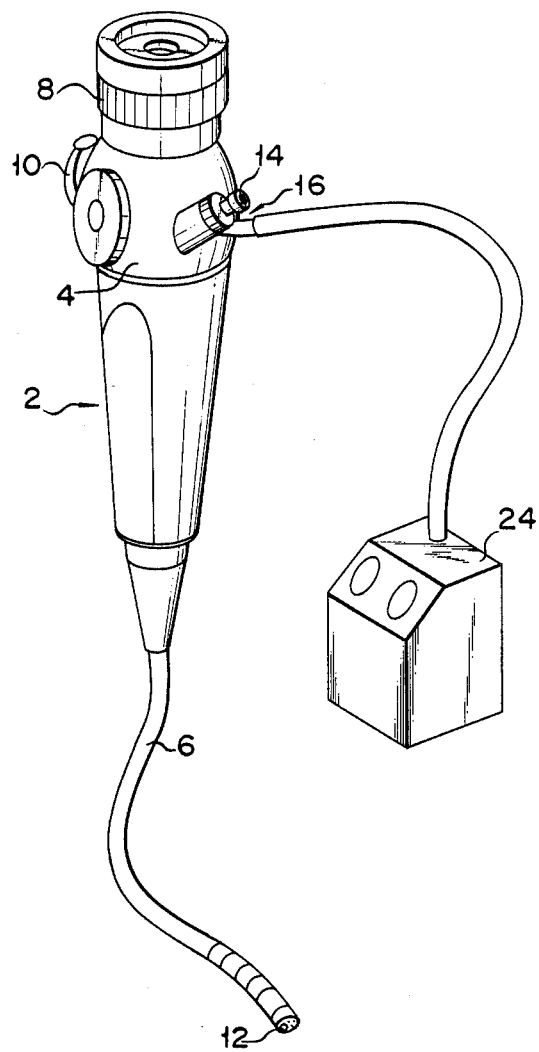
FIG. 1 is a perspective view of an endoscope, fitted with an endoscopic fluid changing device according to the present invention.

Referring first to FIG. 1, there is shown an endoscope, which is fitted with a fluid changing device according to the present invention. Endoscope 2 comprises operating section 4 and insertion section 6. Section 4 is provided with eyepiece portion 8, angle knob 10, fluid changing device 16, and opening portion 14 connected to channel 12, in which a medical instrument is to be inserted.

Figure 2:
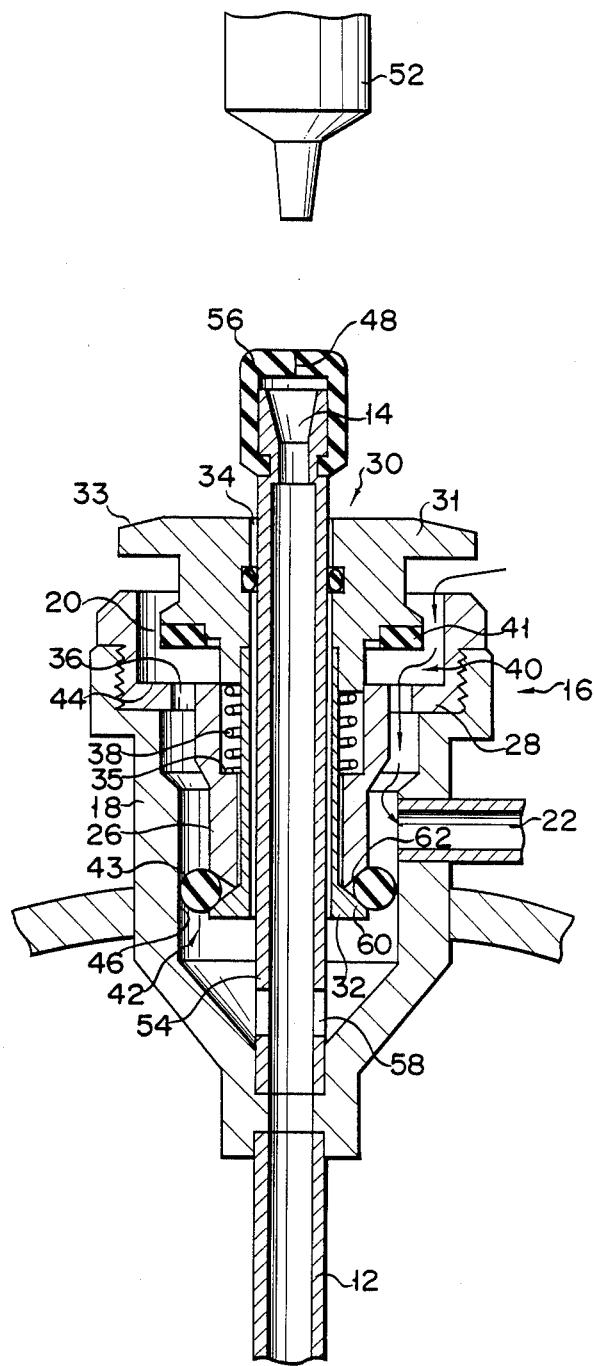
FIGS. 2 and 3 are longitudinal sectional views of an endoscopic fluid changing device according to a first embodiment of the invention.
Figure 3:
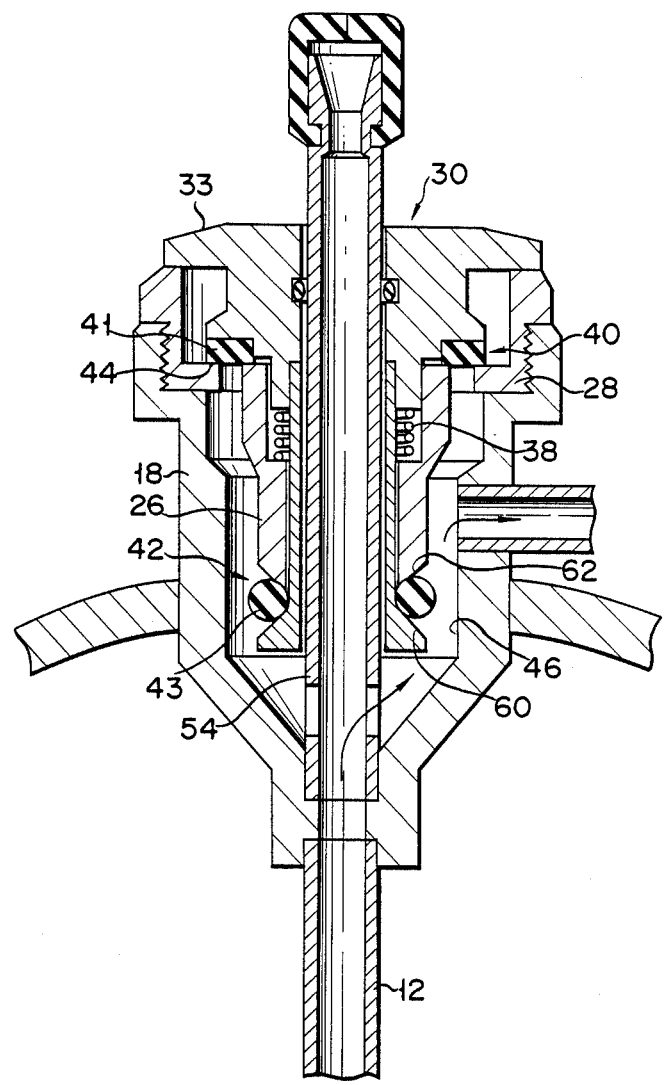

Referring now to FIGS. 2 and 3, there is shown a first embodiment of the fluid changing device of the present invention. As shown in FIG. 2, device 16 comprises cylindrical casing 18, one end of which is connected to channel 12 of operating section 4 of endoscope 2. Spill port 20, opening to the outside of endoscope 2, is formed at the other end portion of casing 18. Suction port 22 is provided at the middle portion of casing 18. It is connected to suction pump 24, which is disposed outside endoscope 2, as shown in FIG. 1. Cylinder 26, having flange 28 at its top portion, is screwed in casing 18 so that a screw portion on the outer peripheral surface of flange 28 engages the inner peripheral surface of casing 18. Piston 30, which includes head 31 and rod portion 32, passes through cylinder 26. Projecting outward from spill port 20 of casing 18, head 31 is formed with flange-shaped operating end portion 33. Flange 28 is formed with a plurality of vent holes 36. Spring 38 is disposed between the lower end face of head 31 of piston 30 and shoulder portion 35 in the middle of cylinder 26. Thus, piston 30 is urged upward by spring 38, so that rod portion 32 is pulled upward. As shown in FIG. 2, moreover, casing 18 contains first and second gate valves 40 and 42, which include elastic valve members 41 and 43, respectively. Member 41 of first valve 40 is formed of a ring-shaped rubber plate, and is attached to the underside of head 31 of piston 30. Member 43 of second valve 42 is formed of a rubber O-ring, and is fitted in a V-shaped groove, which is defined by taper surface 60 on rod portion 32 of piston 30, and taper surface 62 on the lower end portion of cylinder 26. Normally, piston 30 is located in its top position, as shown in FIG. 2, urged by spring 38, so that valve member 41 of first valve 40 is raised. In this state, a first passage, which extends between spill port 20 and suction port 22, is opened. On the other hand, valve member 43 of second valve 42 is extended in the radial direction, so that its outer peripheral surface is closely in contact with valve seat 46, on the inner wall of casing 18. Thus, a second passage, which extends between channel 12 and port 22, is cut off. If piston 30 is pushed in, by pressing operating end portion 33, as shown in FIG. 3, valve member 41 of valve 40 is pressed against valve seat 44. As a result, the first passage, between ports 20 and 22, is cut off. At the same time, valve member 43 of valve 42 is restored to its original shape, so that the second passage, between channel 12 and port 22, is opened.

Thus, valves 40 and 42 are coupled to valve drive means, which includes cylinder 26 and piston 30. When one of the valves closes the passage, corresponding to the position of piston 30, therefore, the other valve is opened.

When piston 30 is not pushed in, that is, when no object is to be sucked from the body cavity, piston 30 is located in its top position by the urging force of spring 38, as shown in FIG. 2. Accordingly, first valve 40 is opened, so that the first passage is opened. On the other hand, second valve 42 is closed, so that the second passage is closed. Thus, suction pump 24, while in operation, can suck in the outside air through spill port 20 and vent holes 36. Since the second passage is completely shut off by second valve 42, undesired sucking from instrument channel 12 can be prevented. Even if a liquid is introduced through opening portion 14, moreover, it can never leak into suction port 22.

In sucking an object from the body cavity, by means of suction pump 24, piston 30 is pushed in, as shown in FIG. 3. Thereupon, first valve 40 is closed, so that the first passage is closed. On the other hand, second valve 42 is opened, so that the second passage is opened. When filth or other matter is sucked from the body cavity, in this state, spill port 20 is completely shut off by first valve 40. Therefore, the matter cannot leak out through port 20, thus ensuring sanitary conditions.

In the operations of the valves, valve members 41 and 43 engage their corresponding valve seats 44 and 46 of cylinder 26, substantially at right angles thereto, without sliding on the seats. Thus, members 41 and 43 can be prevented from being worn away, or from being damaged by the edge portion of suction port 22.

Channel pipe 54 extends substantially through the respective centers of casing 18, cylinder 26, and piston 30, in fluid changing device 16. The lower end portion of pipe 54 is fixed to casing 18, to which instrument channel 12 is connected. The upper end portion of pipe 54, having opening portion 14, projects outward from center hole 34 of piston 30. Opening portion 14 is closed by elastic cap member 56, which is formed with slit 48. For example, syringe 52 can be attached to portion 14. Through hole 58 is formed at the lower portion of pipe 54, whereby channel 12 and the inside of casing 18 are connected fluidly.

In this embodiment, the axes of channel pipe 54, cylinder 26 and piston 30 are arranged in a concentric fashion, whereby fluid changing device 16 can be made compact, and operating section 4 of the endoscope can be made compact.

Figure 4:
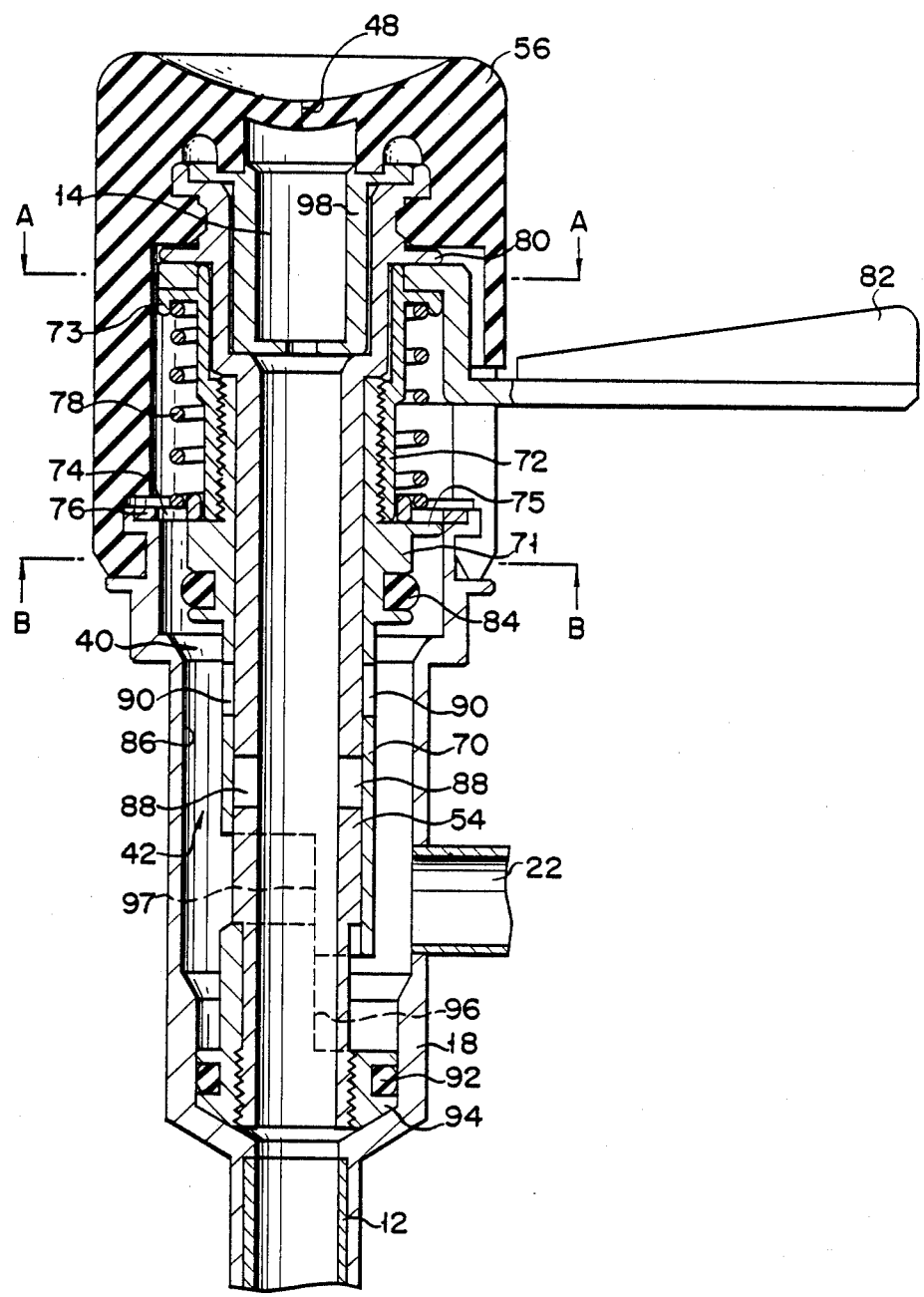
FIG. 4 is a longitudinal sectional view of an endoscopic fluid changing device according to a second embodiment of the invention.
Figure 5:
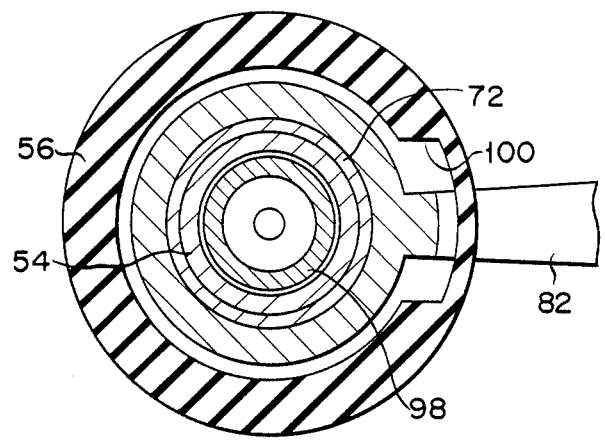
FIG. 5 is a sectional view taken along line A—A of FIG. 4.
Figure 6:
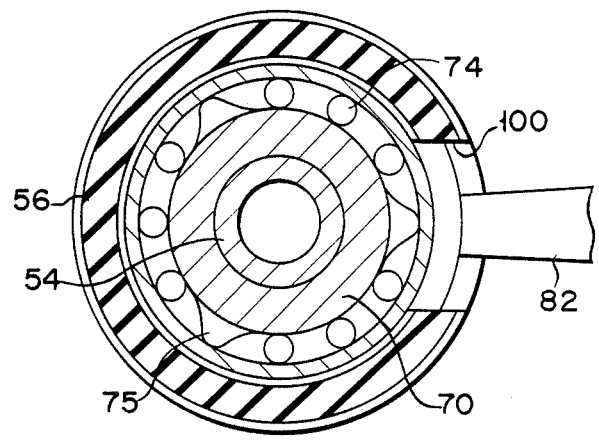
FIG. 6 is a sectional view taken along line B—B of FIG. 4.

Referring now to FIGS. 4, 5 and 6, there is shown a second embodiment of the fluid changing device of the present invention. In this embodiment, slider member 70, which is equivalent to piston 30 of the device of the first embodiment, is fitted on channel pipe 54. A screw portion is formed on the outer peripheral surface of the upper portion of member 70, and connecting pipe 72 is screwed onto the screw portion. Flange portion 73 is formed at the upper portion of pipe 72. Disk 76, having a plurality of vent holes 74, as shown in FIG. 6, is mounted on the top face of casing 18. Coil spring 78 is disposed between disk 76 and portion 73 of member 70. Thus, member 70 and pipe 72 are urged upwardly by spring 78, so that the the upper end of pipe 72 abuts against the underside of upper flange 80, which is formed at the upper portion of channel pipe 54. The top position of slider member 70 is determined in this manner. Operating lever 82 is attached to the upper part of flange portion 73 of connecting pipe 72. The lever is used to depress member 70, against the urging force of spring 78.

Thick portion 71, having three projections 75, is formed at the middle portion of slider member 70. Projections 75, whose tip ends are in contact with the inner peripheral surface of the upper portion of casing 18, serve as guide means for member 70. Ring-shaped elastic valve member 84 is mounted on the lower part of thick portion 71. Member 84, which is equivalent to valve member 41 of the first embodiment, is adapted to lower as member 70 descends. Thus, member 84 comes closely into contact with valve seat 86, on the intermediate portion of the inner wall of casing 18, thereby closing the first passage. A pair of bores 88, facing each other, are formed in that part of channel pipe 54 below valve member 84. Also a facing pair of bores 90 are formed in the lower portion of slider member 70. When member 70 is located in its top position, as shown in FIG. 4, the positions of bores 88 and 90 are shifted vertically, thus preventing the passage of a fluid. When member 70 is moved to its bottom position, the axes of bores 88 and 90 are aligned substantially with one another, thus allowing the passage of the fluid.

The fluid changing device of the second embodiment, as described above, is also provided with first valve 40, including elastic valve member 84 and valve seat 86, and second valve 42, which is formed of first and second bores 88 and 90. As in the case of the first embodiment, the first and second passages are opened or closed alternately.

In the second embodiment, moreover, a screw portion is formed on the outer peripheral surface of the lower end portion of channel pipe 54. Guide member 94, having sealing member 92, is screwed on the screw portion of pipe 54. Disposed in the lower portion of casing 18, member 94 is fixed by frictional resistance between member 92 and casing 18. The upper portion of member 94, having a ring-shaped body, is partially cut off, thus forming guide surface 96 parallel to its axis, as indicated by broken line in FIG. 4. Likewise, the lower portion of slider member 70, also having a ring-shaped body, is partially cut off, thus forming guide surface 97, parallel to its axis and corresponding to surface 96, as indicated by another broken line in FIG. 4. Surfaces 96 and 97 are in contact with each other. Thus, slider member 70, which is allowed to move vertically, is prevented from rotating, by guide member 94.

Slider member 70, pipe 54 and cap member 56 are rotatable relative to casing 18, whereby operating lever 82 can be located in a desired position.

Adapter 98 is attached to top opening portion 14 of channel pipe 54. A syringe can be fitted in the adapter. As shown in FIG. 5, cap member 56, covering the top portion of pipe 54, is formed with recess 100, in which the proximal end portion of operating lever 82 is contained. Slit 48 is formed in the center of the top of member 56. The syringe or some other medical instrument can be inserted into adapter 98 through slit 48.

Figure 7:
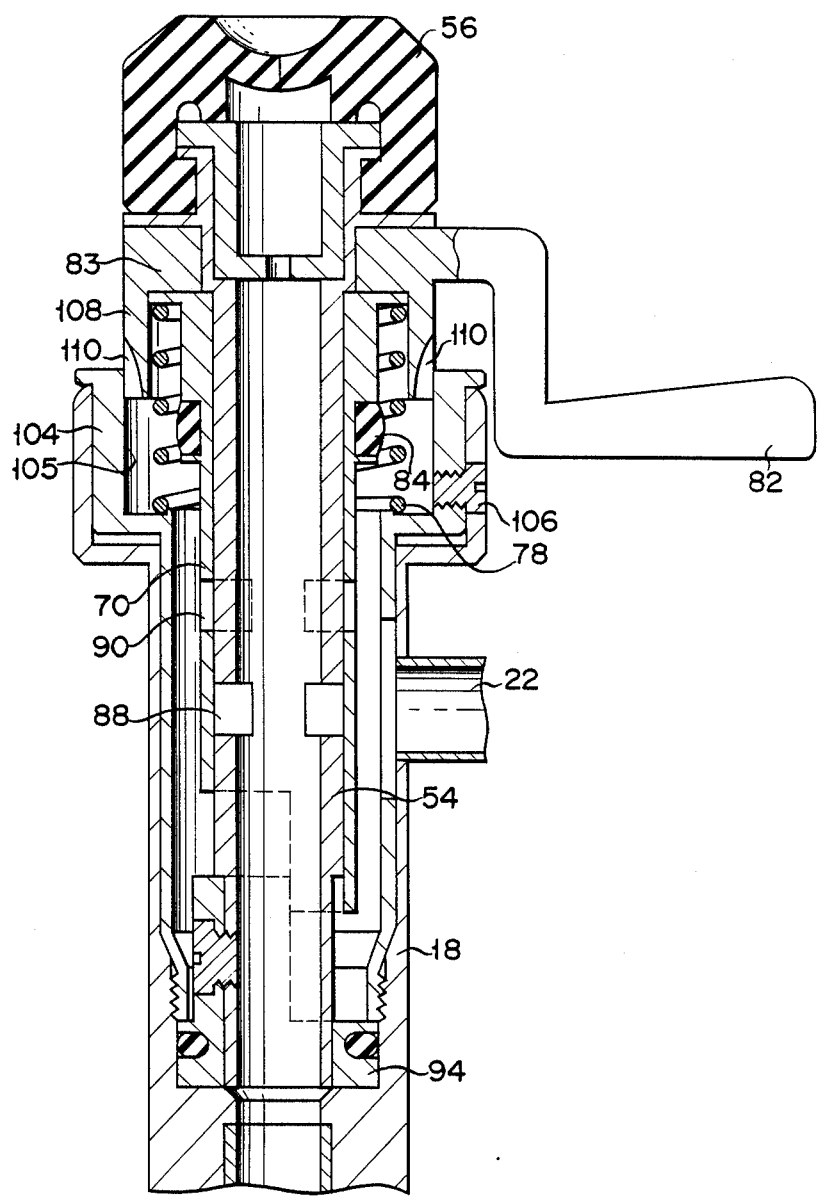
FIG. 7 is a longitudinal sectional view showing a modification of a spill port of the fluid changing device according to the second embodiment of the invention.

FIG. 7 shows a modification of the spill port of the fluid changing device, according to the second embodiment. In this modification, inner cylinder 104 is inserted in casing 18, and fixed by fixing screw 106. Upper bore 105 of cylinder 104 has a diameter greater than the inside diameter of the lower portion of cylinder 104. Ring-shaped projection 108 is formed at the lower part of ring-shaped proximal end portion 83 of operating lever 82. A plurality of vent holes 110 are formed in the lower part of projection 108. Projection 108 is fitted in bore 105. Thus, in this modification, projection 108, with the vent holes therein, serves also as guide means for lever 82.

Figure 8:
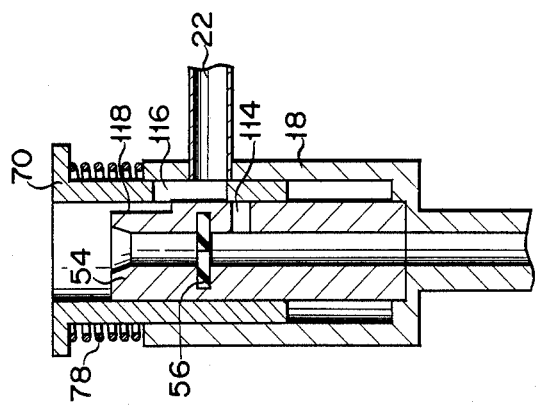
FIG. 8 is a longitudinal sectional view of an endoscopic fluid changing device according to a third embodiment of the invention.

Referring now to FIG. 8, there is shown a third embodiment of the endoscopic fluid changing device of the present invention. In this embodiment, first and second valves 40 and 42 are replaced with a single valve unit, which includes bore 114, formed in the side wall of channel pipe 54, and passage 116 in the side wall of slider member 70. Bore 114 is formed in the middle portion of the side wall of pipe 54, while recess 118 is formed in the upper end portion of the side wall. The side wall of member 70 is formed with passage 116. Passage 116 has a size such that it can fluidly connect suction port 22 with recess 118 when member 70 is in its top position, and with bore 114 when member 70 is in its bottom position. Thus, the suction can be adjusted by moving member 70 up and down. Cap member 56 is disposed in the channel, above bore 114. In consequence, according to this embodiment, the number of components can be reduced.

Figure 9:
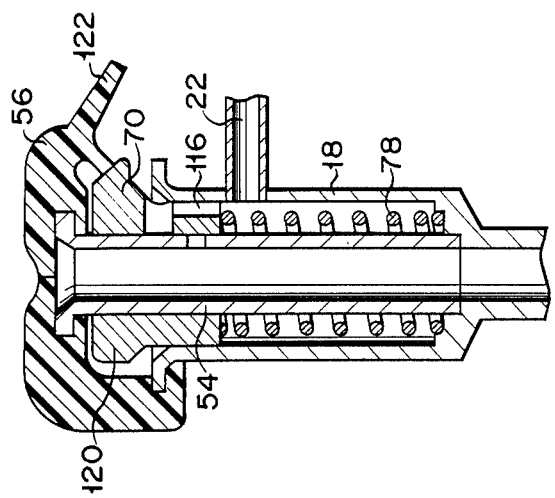
FIG. 9 is a longitudinal sectional view showing a modification of a stopper member of the fluid changing device according to the third embodiment of the invention.

FIG. 9 shows a modification of the cap member of the fluid changing device, according to the third embodiment. In this modification, cap member 56 is formed of, e.g., resin, and is mounted on the respective upper end portions of casing 18 and channel pipe 54, so as to enclose these portions and head portion 120 of slider member 70. One end portion 122 of member 56 extends in the radial direction, as shown in FIG. 9, and serves as an operating lever for driving the slider member. Also according to this modification, the number of components can be reduced.

Figure 10:
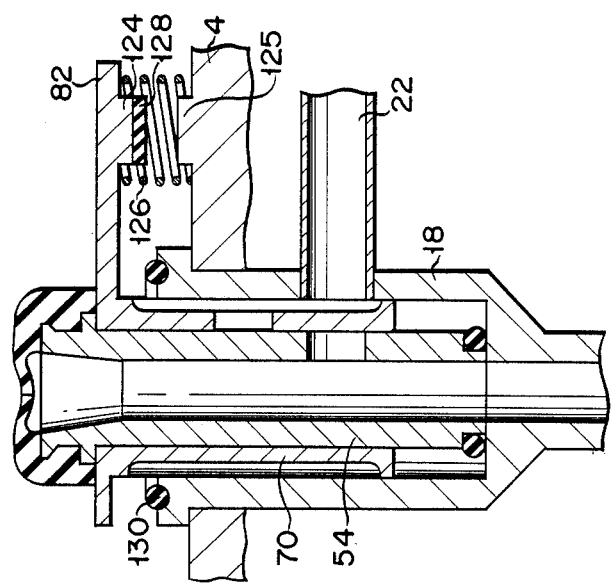
FIG. 10 is a longitudinal sectional view showing a modification of a combination of first valve means and control lever of the fluid changing device according to the third embodiment of the invention.

FIG. 10 shows a modification of a combination of the first valve and operating lever of the fluid changing device, according to the third embodiment. In this modification, operating lever 82, extending in the radial direction, is formed integrally on the upper end portion of slider member 70. Projection 124 is formed on the extreme end portion of lever 82. Spring 126 is interposed between projection 124 and projection 125 on operating section 4. Thus, no spring is provided inside the fluid changing device. Moreover, elastic member 128 is attached to the underside of projection 124. It serves to ease the impact produced when operating lever 82 runs against projection 125 of section 4. First and second valves have the same constructions as those of the foregoing embodiments. O-ring 130 is attached to the upper end portion of casing 18, whereby the inside and outside of the fluid changing device are cut off securely.

Figure 11:
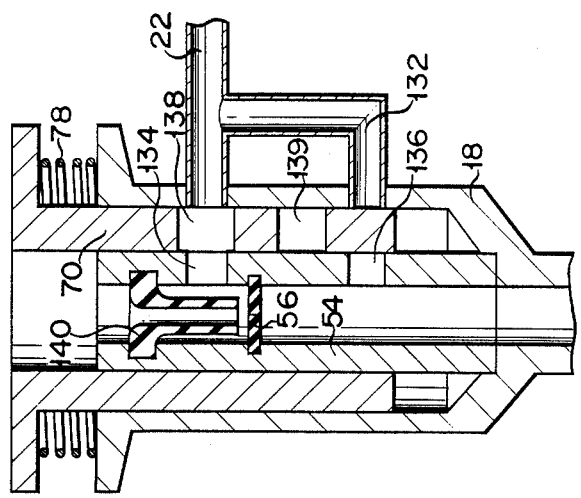
FIG. 11 is a longitudinal sectional view of an endoscopic fluid changing device according to a fourth embodiment of the invention.

Referring now to FIG. 11, there is shown a fourth embodiment of the fluid changing device of the present invention. In this embodiment, second suction port 132 diverges downward from first suction port 22. Channel pipe 54 is formed with first and second through holes 134 and 136, which face first and second suction ports 22 and 132, respectively. Cap member 56 is mounted in the channel, between holes 134 and 136. Thus, hole 134 communicates with the outside of the fluid changing device. First bore 138 is formed in one side wall of slider member 70. It fluidly connects port 22 and hole 134 when member 70 is located in its top position. Moreover, second bore 139 is formed in that portion of the one side wall of member 70 below bore 138. It fluidly connects port 132 and hole 136. Thus, when slider member 70 is moved vertically, the first and second bores alternately open or close their corresponding passages. The suction can be adjusted in this manner. In this embodiment, moreover, guide member 140, formed of an elastic member, guiding a taper portion of a syringe, is attached to the upper portion of channel pipe 54, as shown in FIG. 11. When the syringe is mounted in opening portion 14, first through hole is sufficiently closed by member 140, so that a fluid in the syringe can be supplied without any leakage into the suction device.

Figure 13:
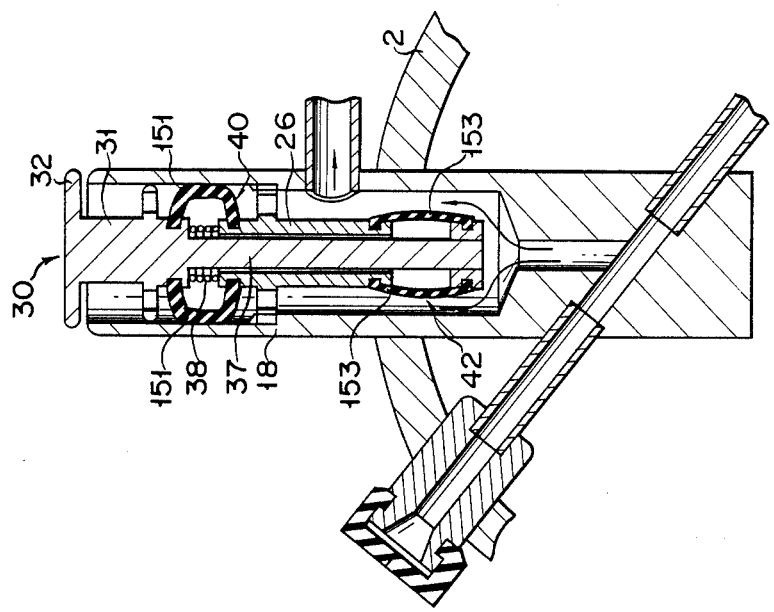
FIGS. 12 and 13 are longitudinal sectional views of an endoscopic fluid changing device according to a fifth embodiment of the invention.
Figure 12:
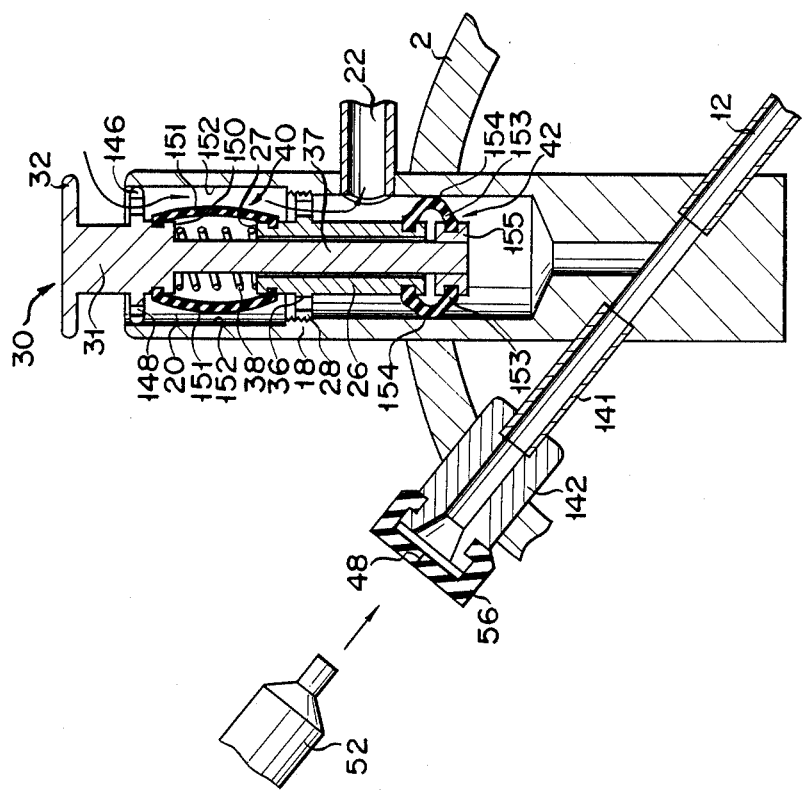

Referring now to FIGS. 12 and 13, there is shown a fifth embodiment of the fluid changing device of the present invention. In this embodiment, casing 18, which is fluidly connected to instrument channel 12, is mounted on operating section 4 of the endoscope. Channel 12 penetrates casing 18 obliquely, and is connected to inlet member 142, which is attached to section 4 by means of coupling 141. Member 142 is fitted with elastic cap member 56, having slit 48, whereby its opening is closed.

Casing 18 is cylindrical in shape, and suction port 22 is provided at the middle portion of the side wall of the casing. Cylinder 26, having flange 28, is mounted in casing 18. Piston 30 has head 31 and rod 37. Rod 37 is passed through cylinder 26, and retainer 155 is fixed to the lower end portion of the rod. The top portion of piston head 31 projects outward from casing 18, through spill port 20 thereof, thus forming flange-shaped operating end portion 33. Lower flange 146 is formed on the lower portion of head 31. The outer peripheral surface of flange 146 is in contact with the inner peripheral surface of casing 18. A plurality of vent holes 36 and 148 are formed in flange 28 of cylinder 26 and flange 146, respectively. Head 31 of piston 30 has shoulder portion 150 at its lower end portion. Spring 38 is disposed between portion 150 and the upper end 27 of cylinder 26. Thus, piston 30 is urged upward by spring 38.

First elastic valve member 151, in the form of a short tube, bridges the space between the lower portion of piston 30 and the upper portion of cylinder 26, so as to surround spring 38. Second elastic valve member 153, also in the form of a short tube, connects the lower portion of cylinder 26 and retainer 155, fixed to piston 30. First valve seat 152 is formed on the inner peripheral surface of the upper portion of casing 18, while second valve seat 154 is formed on the inner peripheral surface of the lower part of casing 18. Thus, first valve 40, including first valve member 151 and seat 152, and second valve 42, including second valve member 153 and seat 154, are formed above and below suction port 22, respectively.

Normally, valve member 151 is stretched by the urging force of spring 38, so that the first passage, extending from spill port 20 to suction port 22, is opened. On the other hand, second valve member 153 is compressed axially, so that its middle portion bulges in the radial direction. Thus, the outer peripheral surface of member 153 abuts against valve seat 154, thereby closing the second passage, which extends between instrument channel 12 and port 22. In sucking filth or the like from the body cavity, operating end portion 33 is pressed to depress piston 30, as shown in FIG. 13.

Thereupon, second valve member 153 is stretched axially, thus opening the second passage. Meanwhile, first valve member 151 is compressed axially, so that its middle portion bulges radially, and its outer peripheral surface abuts against first valve seat 152, thus closing the first passage.

Figure 15:
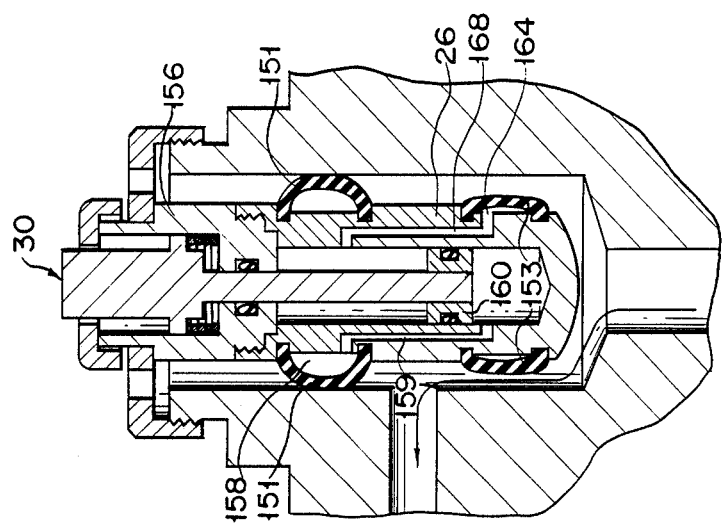
FIGS. 14 and 15 are longitudinal sectional views showing a modification of a valve portion of the device according to the fifth embodiment.
Figure 14:
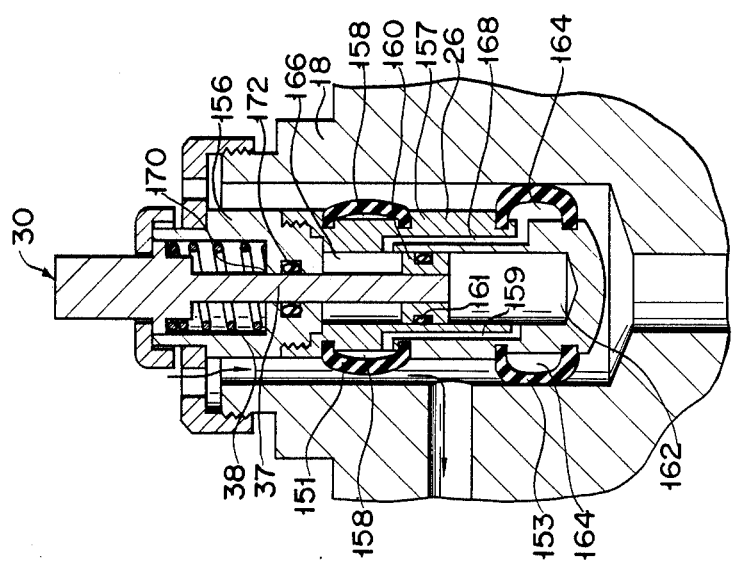

FIGS. 14 and 15 show a modification of the valve section, according to the fifth embodiment. In this modification, cylinder 26, disposed inside casing 18, is formed of upper and lower cylinder members 156 and 157, respectively. Rod 37 of piston 30 is passed through bore 170, which is formed in the bottom portion of upper cylinder member 156. Sealing member 172 is attached to the inner peripheral surface of bore 170, whereby the gap between rod 37 and bore 170 is sealed. Ring-shaped sliding member 160, having sealing member 161 thereon, is mounted on the lower portion of rod 37. First and second valve members 151 and 153 are fitted separately on the outer peripheral surface of cylinder 26. Space 158, defined by valve member 151 and the outer peripheral surface of cylinder 26, is fluidly connected, by means of communication hole 159, to lower cylinder chamber 162, which is defined by lower cylinder member 157 and sliding member 160. Space 164, defined by valve member 153 and the outer peripheral surface of cylinder 26, is fluidly connected, by means of communication hole 168, to upper cylinder chamber 166, which is defined over member 160. Spring 38, which is disposed inside cylinder member 156, urges piston 30 upward.

Thus, as piston 30 moves up and down, sliding member 160 slides inside lower cylinder member 157, so that a fluid, sealed in member 157, is fed alternately into spaces 158 and 164. Accordingly, valve members 151 and 153 expand or contract alternately. As a result, in response to the action of piston 30, the valves are opened and closed, so that the first and second passages are opened and closed, correspondingly.

According to the fifth embodiment and the aforementioned modification thereof, the valve members never slide on the valve seats at all, and hence, are improved substantially in durability.

In connection with the several embodiments described above, the fluid changing device of the present invention is designed so as to change the mode of suction by a suction pump. However, the invention is not limited to such an arrangement, and may be applied also to fluid adjustment, for the feed of air, water, gas, etc., for example.

According to the present invention, as described in detail herein, filth or other matter, sucked from the body cavity, can be prevented from scattering from the spill port. Thus, an operator can operate the device in a sanitary manner, without soiling his fingers with such matter. When in a nonsuction state, the suction in the instrument channel can be stopped entirely, thus ensuring safety. In feeding a liquid, moreover, the liquid cannot leak into the suction pump. Further, the valve members and valves seats are less liable to wear or damage, enjoying improved durability. Furthermore, the manufacturing costs of the fluid changing device can be reduced.

What is claimed is:

1. An endoscopic fluid changing device which is associated with an endoscope having an instrument channel, comprising:
    a cylindrical casing having a suction port, in the side wall thereof;

a channel pipe provided in the center of the casing, and having an opening at the upper end portion thereof, the lower end portion of said channel pipe being connected to the instrument channel, extending to the distal end portion of the endoscope;

a cap member covering the opening of the channel pipe;

a piston disposed between the casing and the channel pipe, and capable of vertical motion;

a spring for urging the piston upward;

first valve means provided at the upper portion of the piston, and adapted to open or close a first passage as the piston is operated, said first passage extending from the suction port to the outside of the casing; and second valve means provided at the lower portion of the piston, and adapted to close or open a second passage, in contrast with the first passage, as the piston is operated, said second passage extending from the suction port to the instrument channel.

2. The endoscopic fluid changing device according to claim 1, wherein said cap member is formed of an elastic member, having a slit in the central portion thereof.

3. The endoscopic fluid changing device according to claim 1, further comprising a cylinder mounted inside the casing, and including a flange portion with a plurality of through holes, whereby said piston is guided.

4. The endoscopic fluid changing device according to claim 3, wherein said first valve means includes a valve seat formed on the top surface of the flange portion, and a ring-shaped valve member attached to the piston; and said second valve means includes a valve seat formed on the inner peripheral surface of the lower portion of the casing, and an O-ring disposed in a V-shaped groove, said groove being defined by a taper surface formed at the lower end portion of the cylinder, and another taper surface formed at the lower end portion of the piston.

5. The endoscopic fluid changing device according to claim 1, wherein said first valve means includes a valve seat formed on the inner peripheral surface of the casing, and a ring-shaped valve member attached to the piston; and said second valve means includes a bore formed in the channel pipe, and another bore formed in the piston.

6. The endoscopic fluid changing device according to claim 5, further comprising a guide member mounted on the lower portion of the channel pipe, and adapted to prevent the piston from rotating, but allows the piston to move vertically.

7. The endoscopic fluid changing device according to claim 5, further comprising an operating lever attached to the upper end portion of the piston, and used to drive the piston.

8. The endoscopic fluid changing device according to claim 1, wherein said first and second valve means are formed of a single valve unit, including a bore formed in the side wall of the channel pipe, and a passage formed in the side face of the piston, said passage being adapted to fluidly connect the suction port and the outside of the casing, when the piston is located in its top position, and to fluidly connect the suction port and the bore, when the piston is located in its bottom position.

9. The endoscopic fluid changing device according to claim 8, wherein one end portion of said cap member extends radially, thus constituting an operating lever for driving the piston.

10. The endoscopic fluid changing device according to claim 1, wherein said piston includes a flange portion formed integrally on the upper end portion thereof; said first valve means includes a valve seat formed on the underside of the flange portion, and a valve member attached to the upper end face of the casing; and said second valve means includes a bore formed in the lower portion of the side face of the channel pipe, and another bore formed in the middle portion of the piston.

11. The endoscopic fluid changing device according to claim 10, further comprising an operating lever formed integrally with the flange portion of the piston.

12. The endoscopic fluid changing device according to claim 1, wherein said first valve means includes the suction port, a first bore formed in the middle portion of the piston, and a first through hole facing the suction port in the side wall of the channel pipe; said second valve means includes a second suction port formed in the lower portion of the side wall of the casing and diverging from the suction port, a second bore formed in the lower portion of the side wall of the piston, and a second through hole facing the second suction port in the side wall of the casing; and said cap member is attached between the first and second through holes.

13. An endoscopic fluid changing device which is associated with an endoscope having an instrument channel, comprising:

a cylindrical casing having a suction port, in the side wall thereof;

a cylindrical having a flange portion formed with a plurality of vent holes, and mounted inside the casing by means of the flange portion;

a piston having a rod portion and capable of vertical motion, with the rod portion passed through the cylinder;

a spring for urging the piston upward;

first valve means provided at the upper portion of the cylinder, and adapted to open or close a first passage as the piston is operated, said first passage extending from the suction port to the outside of the casing, via the vent holes; and second valve means provided at the lower portion of the cylinder, and adapted to close or open a second passage, in contrast with the first passage, as the piston is operated, said second passage extending from the suction port to the instrument channel.

14. The endoscopic fluid changing device according to claim 13, wherein said first and second valve means each include a tubular elastic valve member, and a valve seat formed on the inner surface of the casing.

15. The endoscopic fluid changing device according to claim 14, wherein said valve members are stretched or compressed by the vertical motion of the piston, thereby opening or closing the valve means.

16. The endoscopic fluid changing device according to claim 14, wherein a fluid, sealed in the cylinder, moves as the piston is operated, thereby contracting or expanding the valve members so that the valve means is opened or closed.

* * * * *